US006219404B1

(12) United States Patent
Thomson et al.

(10) Patent No.: US 6,219,404 B1
(45) Date of Patent: Apr. 17, 2001

(54) METHOD OF DETERMINING IF AN ALLOY ARTICLE HAS ANY REMAINING WORKING LIFE

(75) Inventors: Rachel C Thomson, Coventry; Marco J Starink, Southampton, both of (GB)

(73) Assignee: Rolls-Royce plc, London (GB)

( * ) Notice: Subject to any disclaimer, the term of this patent is extended or adjusted under 35 U.S.C. 154(b) by 0 days.

(21) Appl. No.: 09/398,431

(22) Filed: Sep. 17, 1999

(30) Foreign Application Priority Data

Sep. 26, 1998 (GB) .................................................. 9820918

(51) Int. Cl.$^7$ ..................................................... G01N 23/20

(52) U.S. Cl. .................................................................. 378/72

(58) Field of Search ......................................... 378/71, 72

(56) References Cited

U.S. PATENT DOCUMENTS 5,148,458 * 9/1992 Ruud ...................................... 378/72

FOREIGN PATENT DOCUMENTS 242 425   10/1987   (EP) .
2201 733   9/1988   (GB) .

* cited by examiner

*Primary Examiner*—Craig E. Church
(74) *Attorney, Agent, or Firm*—W. Warren Taltavull; Manelli, Denison & Selter PLLC

(57) ABSTRACT

A method of determining if an alloy article (28) has any remaining working life comprises taking a sample from an alloy article (28) and removing all metal matrix material from the sample to leave the carbide particles. The carbide particles are analysed using x-ray diffraction to determine the ratio of the amount of the $M_{23}C_6$ carbide phase to the amount of the MC carbide phase. This ratio is compared with a database, containing the ratio of the amount of the $M_{23}C_6$ carbide phase to the amount of the MC carbide phase as a function of temperature of heat treatment and time of heat treatment, to determine the temperature of heat treatment and the time of heat treatment of the sample of the alloy article (28). This is compared with a database of heat treatment temperatures and associated heat treatment times corresponding to the full working life of the alloy article (28) to determine if the alloy article (28) has any remaining working life.

13 Claims, 3 Drawing Sheets

METHOD OF DETERMINING IF AN ALLOY ARTICLE HAS ANY REMAINING WORKING LIFE

The present invention relates generally to a method of determining if an alloy article has any remaining working life, particularly to a method of determining if a nickel superalloy article for gas turbine engines has any remaining working life.

One of the main difficulties in determining if gas turbine engine components, particularly turbine blades and turbine vanes, have any remaining working life is that the gas turbine engines may be operated with different operating cycles. Hence a prediction of the service life of a gas turbine engine component is often made with little, or no, knowledge of the history of the use of the gas turbine engine component.

One known method of determining if gas turbine engine components have any remaining working life performs creep tests on a representative number of components. However, the resulting scatter in the test data makes the remaining working life estimate to be conservative.

An additional problem is that it is difficult to make allowances for the starting conditions of the gas turbine engine components. There may be a considerable variation in the initial microstructure of the gas turbine engine components because of the variability of the casting process.

Accordingly the present invention seeks to provide a method of determining if an alloy article has any remaining working life which reduces or overcomes the above mentioned problems.

Accordingly the present invention provides a method of determining if an alloy article has any remaining working life comprising the steps of:

(a) taking at least one sample from an alloy article, (b) removing substantially all metal matrix material from the at least one sample to leave the carbide particles, (c) analysing the carbide particles using x-ray diffraction, identifying the x-ray peaks of the main carbide phases from the x-ray diffraction spectra, (d) determining the ratio, or difference, of the amount of a first carbide phase to the amount of a second carbide phase, (e) providing a database containing the ratio, or difference, of the first carbide phase to the second carbide phase as a function of temperature of heat treatment and time of heat treatment, (f) comparing the ratio, or difference, of the amount of the first carbide phase to the amount of the second carbide phase determined in step (d) with the database in step (e) to determine the temperature of heat treatment and the time of heat treatment of the sample of the alloy article, (g) comparing the temperature of heat treatment and the time of heat treatment of the sample of the alloy article determined in step (f) with a plurality of different heat treatment temperatures and associated heat treatment times corresponding to the full working life of the alloy article to determine if the alloy article has any remaining working life.

Preferably step (d) comprises determining the ratio, or difference, of the amount of the $M_{23}C_6$ carbide phase to the amount of the MC carbide phase.

Step (d) may comprise determining the ratio, or difference, of the amount of the $M_{23}C_6$ carbide phase to the amount of the $M_6C$ carbide phase.

Step (d) may comprise determining the ratio, or difference, of the amount of the $M_6C$ carbide phase to the amount of the MC carbide phase.

Preferably step (d) comprises determining the ratio of the integrated intensity of the x-ray peak of the first carbide phase to integrated intensity of the x-ray peak of the second carbide phase.

Step (b) comprises dissolving substantially all the metal matrix material from the at least one sample in an electrochemical cell to leave the carbide particles.

Step (b) comprises dissolving substantially all the metal matrix material in an electrochemical cell having a solution comprising hydrochloric acid, tartaric acid and methanol.

Preferably the alloy article is a nickel base superalloy, a cobalt base superalloy or an iron base superalloy.

Preferably the alloy article is a turbine blade or a turbine vane.

Preferably step (a) comprises removing the sample from the leading edge of the turbine blade or turbine vane.

Preferably step (a) comprises removing the sample from a predetermined position on the leading edge of each turbine blade or each turbine vane.

The alloy article may comprise an alloy comprising 10 wt % Co, 9 wt % Cr, 5.5 wt % Al, 10 wt % W, 2.5 wt % Ta, 1.5 wt % Ti, 1.5 wt % Hf, 0.15 wt % C and the balance Ni plus incidental impurities.

The alloy article may comprise an alloy comprising 16 wt % Cr, 8.5 wt % Co, 3.4 wt % Al, 2.6 wt % W, 1.7 wt % Ta, 3.4 wt % Ti, 1.7 wt % Mo, 0.8 wt % Nb, 0.11 wt % C and the balance Ni plus incidental impurities.

The alloy article may comprise 8.3 wt % Cr. 10 wt % Co, 0.7 wt % Mo, 10 wt % W, 3 wt % Ta, 5.5 wt % Al, 1 wt % Ti, 0.14 wt % C, 1.5 wt % Hf and the balance Ni plus incidental impurities.

The present invention will be more fully described by way of example with reference to the accompanying drawing, in which.

Figure 1:
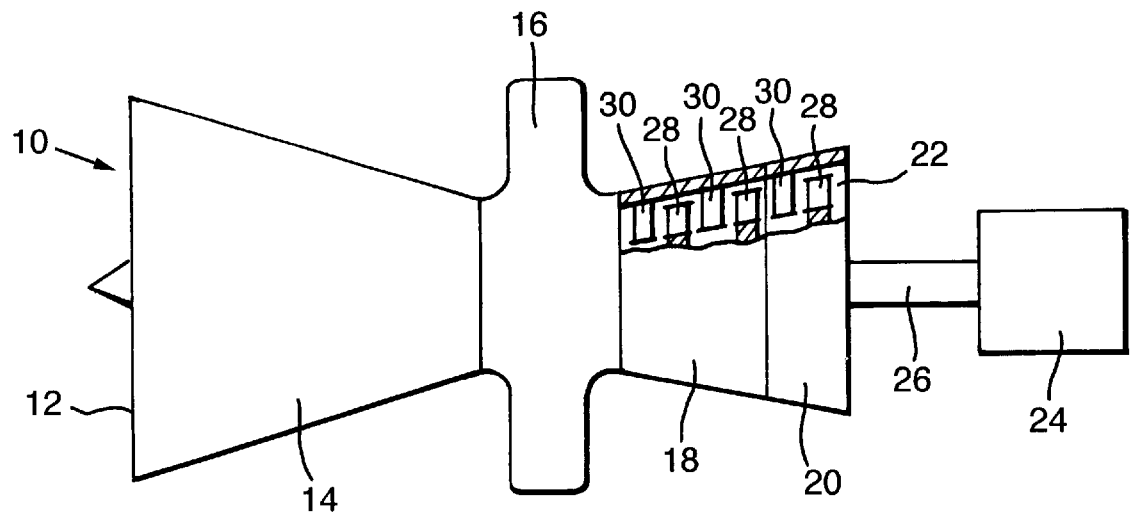
FIG. 1 is a view of an industrial gas turbine engine having turbine blades and turbine vanes.

An industrial gas turbine engine 10, shown in FIG. 1, comprises in axial flow series an inlet 12, a compressor section 14, a combustion chamber assembly 16, a turbine section 18, a power turbine section 20 and an exhaust 22. The turbine section 18 is arranged to drive the compressor section 14 via one or more shafts (not shown). The power turbine section 20 is arranged to drive an electrical generator 24 via a shaft 26, alternatively the power turbine section may drive a pump or a propeller. The operation of the gas turbine engine is quite conventional and will not be discussed further.

Figure 2:
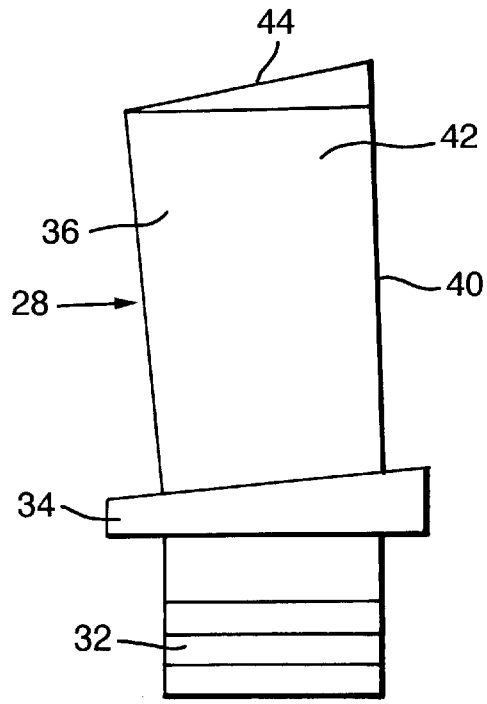
FIG. 2 is a perspective view of a turbine blade shown in FIG. 1.

The turbine section 18 and the power turbine section 20 comprises turbine blades 28 and turbine vanes 30, a turbine blade 28 is shown more clearly in FIG. 2. The turbine blade 28 comprises a root portion 32, a platform portion 34 and an aerofoil portion 36. The aerofoil portion 36 has a leading edge 38, a trailing edge 40, a concave pressure surface 42 and a convex suction surface 44.

The turbine blades 28 and turbine vanes 30 are generally cast from nickel based superalloys. The turbine blades 28 or turbine vanes 30 may be conventionally cast or directionally solidified or cast as single crystals.

The turbine blades, or turbine vanes, may be provided with environmental protective coatings and/or thermal barrier coatings.

Conventionally cast and directionally solidified nickel based superalloy components, turbine blades 28 and turbine vanes 30 contain carbon, which leads to the precipitation of a number of carbide phases within the microstructure.

It is desirable, periodically during servicing of gas turbine engines, to know if the turbine blades 28 or turbine vanes 30 in the gas turbine engine 10 have any remaining working life and how much remaining working life the turbine blades 28 or turbine vanes 30 have. If the turbine blades 28 or turbine vanes 30 do not have any remaining working life, they must be replaced with new turbine blades 28 or turbine vanes 30. If the turbine blades 28 or 30 have some remaining working life they may still be used until their full working life has expired.

In order to determine if the turbine blades 28, or turbine vanes 30, have any remaining working life a number of samples of the alloy from which the turbine blades 28 and turbine vanes 30 are cast are given the same heat treatment as the turbine blades 28, or turbine vanes 30. The samples were subsequently heat treated at a range of temperatures that the turbine blades 28 and turbine vanes 30 are likely to experience in operation. Some of the samples at each heat treatment temperature were examined at 50 day intervals up to a period of 250 days. However samples may be examined at any suitable time interval and for any time duration.

The samples taken at each heat treatment temperature for each 50 day time period were examined by firstly removing all the metal matrix material from the samples to leave only the carbide phases in the samples. The metal matrix material is removed by placing the samples one at a time in an electrochemical cell and dissolving all the metal matrix material to leave the carbide phases. The electrochemical cell is set up to dissolve the gamma and gamma prime phases in the nickel superalloy, that is metal and intermetallic phases. The electrochemical cell contained a solution of 10% hydrochloric acid, 1% tartaric acid and methanol and was operated with a current of 0.02 A for up to 16 hours. The electrochemical cell may be operated using other suitable solutions and currents. The sample may be agitated by placing the electrochemical cell in an ultrasonic bath to ultrasonically agitate the sample. The surface of the sample is periodically washed with methanol. The carbide phases, or carbide phase particles, are removed from the solution in the electrochemical cell by filtering the solution and collecting the carbide phase particles on a filter paper, for example an amorphous glass microfiber filter paper.

The carbide phase particles from each sample are examined in an x-ray diffractometer, for example a Philips Xpert diffractometer with a copper x-ray tube operated at 40 kV and 40 mA. Each sample was scanned over 2θ values ranging from 10–140°. The widths of the divergence and receiving slits were 1° and 0.1° respectively.

The x-ray diffraction spectra of each sample was analysed using conventional techniques, for example Philips Profit software, to determine the ratios, or differences, of the amounts of different carbide phases present by integrating the intensity of the x-ray peaks corresponding to the different carbide phases. Thus a database containing the ratios, or differences, of the amounts of different carbide phases at different heat treatment temperatures for different heat treatment times is produced.

In order to determine if the turbine blades 28, or turbine vanes 30, have any remaining working life one or more samples are taken from the turbine blades 28, or turbine vanes 30, which have operated in the turbine 18, or turbine 20, of the gas turbine engine 10 for an unknown period of time and at an unknown operating temperatures. Preferably the samples are removed from a predetermined position at the leading edge of each turbine blade 28, or turbine vane 30.

All the metal matrix material from the samples of the turbine blades 28, or turbine vanes 30, is removed to leave only the carbide phases in the samples. The metal matrix material is removed by placing the samples one at a time in an electrochemical cell and dissolving all the metal matrix material to leave the carbide phases. The electrochemical cell contained a solution of 10% hydrochloric acid, 1% tartaric acid and methanol and was operated with a current of 0.02 A for up to 16 hours. The electrochemical cell may be operated using other suitable solutions and currents. The sample may be agitated by placing the electrochemical cell in an ultrasonic bath to ultrasonically agitate the sample. The surface of the sample is periodically washed with methanol. The carbide phases, or carbide phase particles, are removed from the solution in the electrochemical cell by filtering the solution and collecting the carbide phase particles on a filter paper, for example an amorphous glass microfiber filter paper.

The carbide phase particles from each sample are examined in an x-ray diffractometer, for example a Philips Xpert diffractometer with a copper x-ray tube operated at 40 kV and 40 mA. Each sample was scanned over 2θ values ranging from 10–140°. The widths of the divergence and receiving slits were 1° and 0.1° respectively.

The x-ray diffraction spectra of each sample was analysed using conventional techniques, for example Philips Profit software to determine the ratios, or differences, of the amounts of different carbide phases present by integrating the intensity of the x-ray peaks corresponding to the different carbide phases.

The ratio, or difference, of the amount of a first carbide phase to the amount of a second carbide phase in the samples is compared with the database of ratios, or K differences, of the amount of the first carbide phase to the second carbide phase to determine the temperature of heat treatment and the time of heat treatment of the sample of the turbine blade 28, or turbine vane 30.

A model is provided to assist with the determination of unknown metal temperatures by comparison with the experimental database. The model contains a description of the reaction kinetics of the carbide phases during heat treatment at various heat treatment temperatures for various heat treatment times. The model embodies in it a description of the thermodynamic equilibrium state of the carbide phases in the alloy as a function of temperature. The model, which is based on fundamental scientific principles, enables the fitting of curves to the experimental points in the database using empirical constants to enable interpolation to temperatures for which no experimental data exists, for example in between the temperatures at which the samples in the database were exposed. Alternatively, the use of standard curve fitting techniques to the experimental data would also be possible.

The temperature of heat treatment and the time of heat treatment of the sample of the turbine blade 28, or turbine vane 30, is compared with a plurality of different heat treatment temperatures and associated heat treatment times corresponding to the full working life of the turbine blade 28, or turbine vane 30, to determine if the turbine blade 28, or turbine vane 30, has any remaining working life. If it is determined that the turbine blades 28, or turbine vanes 30, have some remaining life, they may be left in the turbine 18, 20 or the turbine blades 28 and/or turbine vanes 30 may removed from the turbine 18, 20 and the existing coating is stripped and a new coating is applied an the turbine blades 28, or turbine vanes 30, are put back into the turbine 18, 20.

It is to be noted that the present invention is applicable to the metal matrix material of the article and not any environmental protective coating or thermal barrier coating applied to the article.

EXAMPLE 1

Samples of MARM-002 were heat treated by heat treating at a temperature of 1190° C. for 15 minutes, followed by a heat treating at a temperature of 870° C. for 18 hours. This is the normal heat treatment applied to MARM-002 components before service use.

Some of the samples were heat treated at a temperature of 700° C. for 50 days, 100 days, 150 days, 200 days and 250 days respectively. Some of the samples were heat treated at a temperature of 800° C. for 50 days, 100 days, 150 days, 200 days and 250 days respectively. Some of the samples were heat treated at a temperature of 900° C. for 50 days, 100 days, 150 days, 200 days and 250 days respectively. Some of the samples were heat treated at a temperature of 1000° C. for 50 days, 100 days, 150 days, 200 days and 250 days respectively.

Each of the samples was placed in an electrochemical cell to remove all the metal matrix material from the carbide phase particles. The carbide phase particles from each sample were analysed by x-ray diffraction to determine the ratio of the amount of a first carbide phase to the amount of a second carbide phase to produce the database of ratios of amounts of different carbide phases at different heat treatment temperatures for different heat treatment times.

In particular it has been found that in MARM-002 that there are three main types of carbide phases present, these are $M_6C$, $M_{23}C_6$ and MC. The $M_6C$ carbide phase has a composition of approximately $(W_{0.45}, Cr_{0.25}, Ni_{0.2}, Co_{0.1})_6C$, the $M_{23}C_6$ carbide phase has a composition of approximately $(Cr_{20}, W_2, Co)C_6$ and the MC carbide phase a composition of approximately $(Ti,Ta,Hf,W,Zr)C$, however, there are several compositions for MC.

Figure 3:
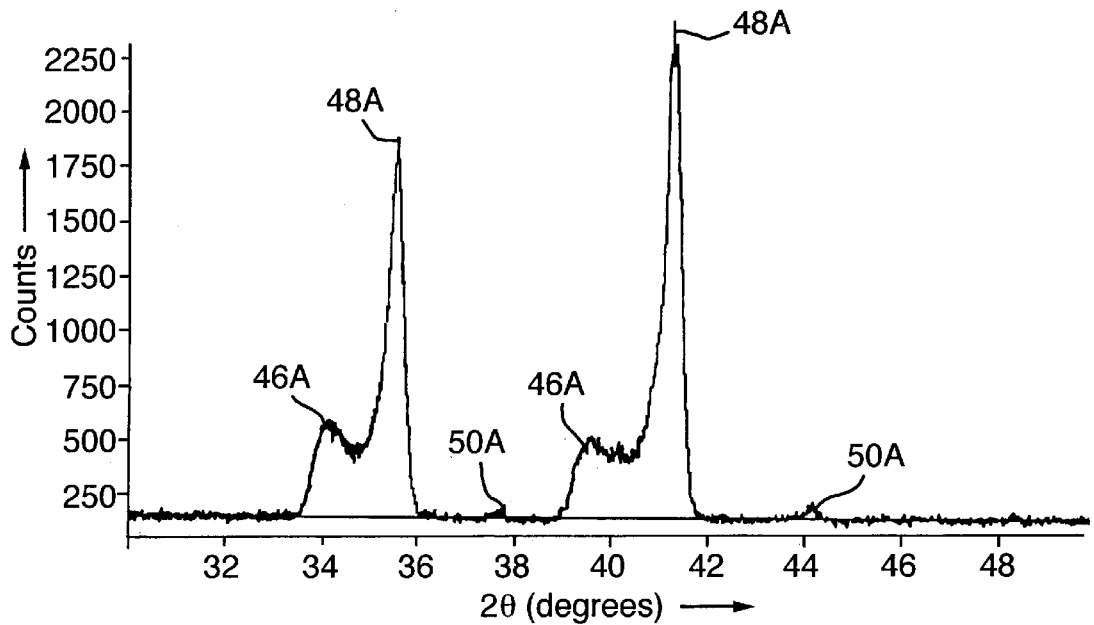
FIG. 3 is an x-ray spectra for a MARM-002 alloy after normal pre-service commercial heat treatment for the intensity of x-rays against the 2θ angles.
Figure 4:
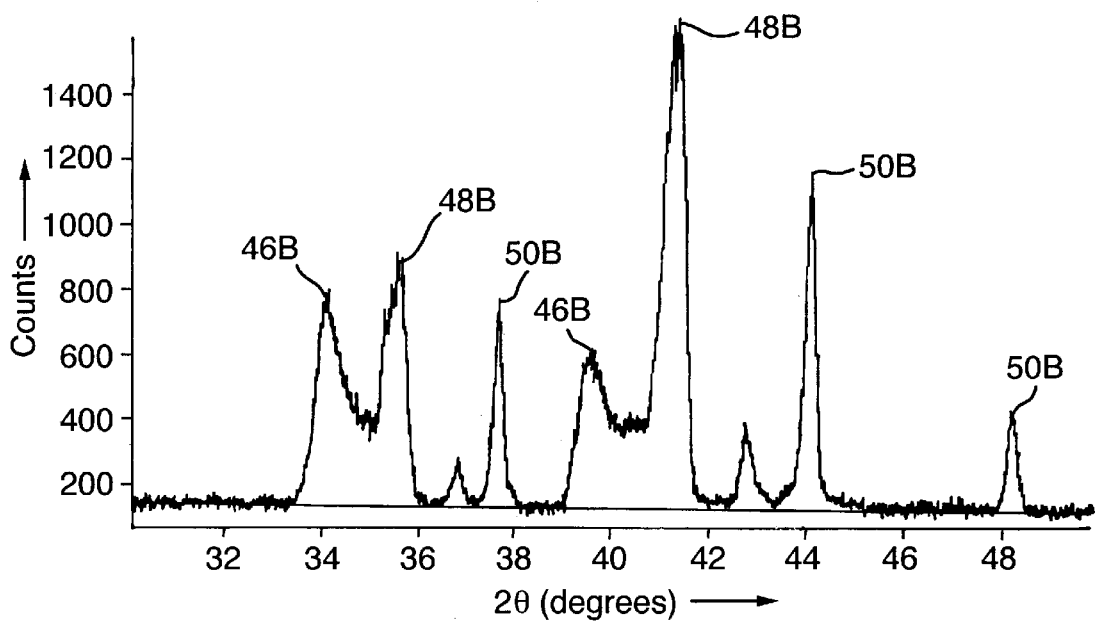
FIG. 4 is an x-ray spectra for a MARM-002 alloy after subsequent/heat treatment at a temperature of 900° C. for 250 days for the intensity of x-rays against the 2θ angles.
Figure 5:
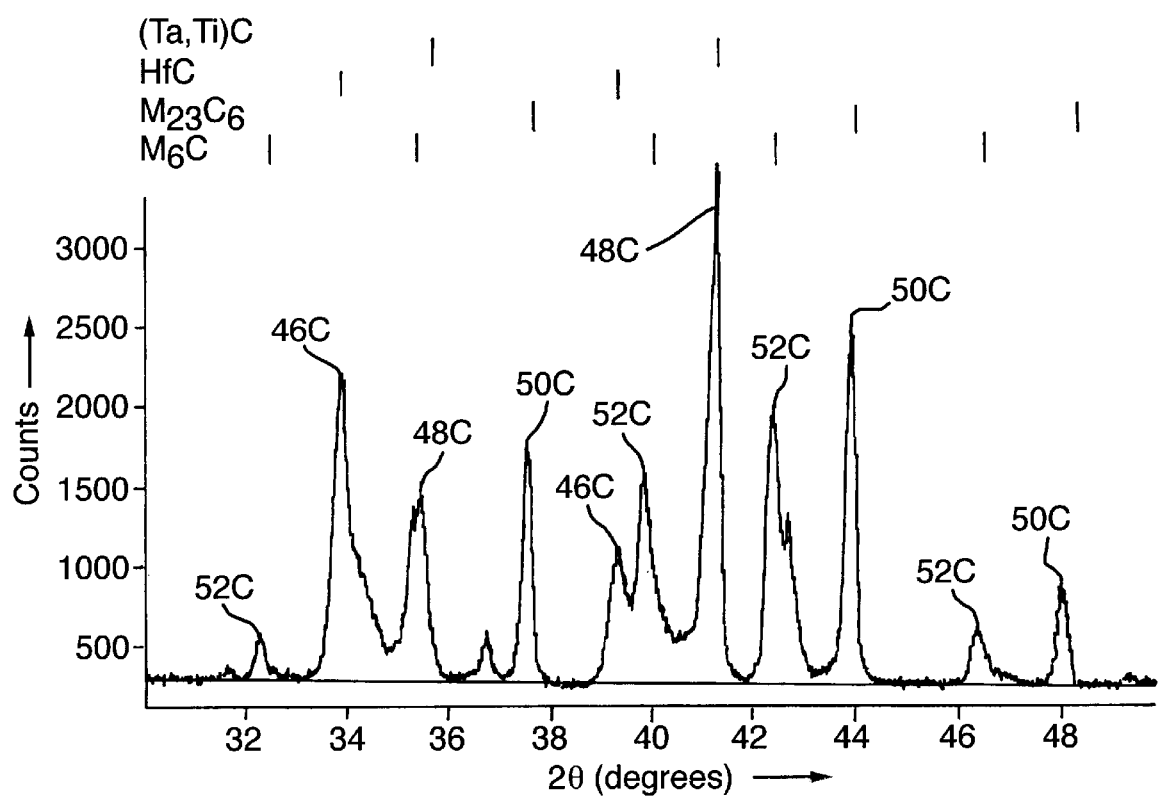
FIG. 5 is an x-ray spectra for a MARM-002 alloy after subsequent heat treatment at a temperature of 1000° C. for 250 days for the intensity of x-rays against the 2θ angles.
Figure 6:
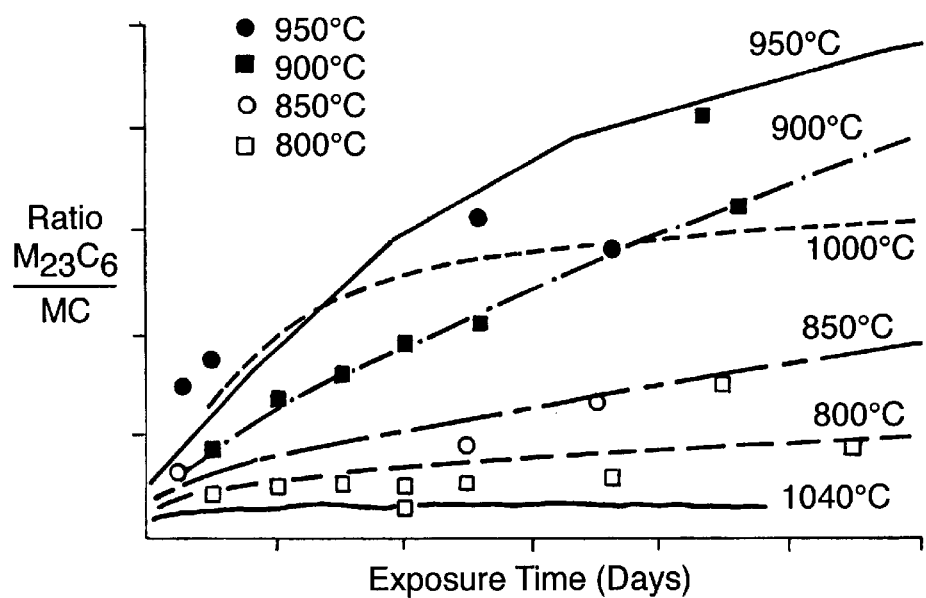
FIG. 6 is a graph showing the ratio of the amount of $M_{23}C_6$ carbide phase to the amount of the MC carbide phase in a MARM-002 during exposure at temperatures between 800° C. and 1100° C.

It has been found that on heat treatment the amount of $M_{23}C_6$ progressively increases on exposure to heat treatment at temperatures of 800° C. and above. As the temperature approaches the maximum stability limit of approximately 1020° C. the amount of $M_{23}C_6$ progressively decreases. On heat treatment at temperatures of 950° C. and above the amount of $M_6C$ increases. It is seen by comparing FIGS. 3, 4 and 5 that the peaks of the x-ray spectra corresponding to the $M_{23}C_6$ carbide phase 50A, 50B and 50C respectively and the peaks of the x-ray spectra corresponding to the $M_6C$ carbide phase 52C generally increase with heat treatment temperature. Conversely, the amount of MC carbide phase progressively decreases on heat treatment at temperatures of 800° C. and above. It can also be seen from FIGS. 3, 4 and 5 that there is a switch over in the intensities of the different types of MC carbide phase peaks 46A, 46B and 46C corresponding to hafnium rich MC carbide phase and 48A, 48B and 48C corresponding to a titanium/tantalum rich MC carbide phase with increasing temperature.

In the case of MARM-002 the ratio of the amount of the $M_{23}C_6$ carbide phase to the amount of the MC carbide phase is determined for temperatures above 750° C. to 900° C. and it may be possible to determine the ratio of the amount of the $M_6C$ carbide phase to the amount of the MC carbide phase above 900° C. It may also be possible to determine the ratio of the amount of the $M_6C$ carbide phase to the amount of the $M_{23}C_6$ carbide phase above 900° C. The ratio is determined using carefully selected peaks in the x-ray spectra to ensure that the peak has minimum error introduced due to contributions from overlapping peaks, but also that the peak has maximum intensity.

Samples were taken from the leading edges of MARM-002 turbine blades and were processed in an electrochemical cell to leave the carbide phase particles. The carbide phase particles were analysed by x-ray diffractometer and the ratio of the amount of the $M_{23}C_6$ carbide phase to the amount of the MC carbide was determined from the x-ray spectra. These ratios were compared to those in the database to determine the heat treatment temperature and heat treatment time of the turbine blade 28, or turbine vane 30, samples which gives an indication of the amount of the working life used at that temperature of heat treatment.

It has been found that this provides an accuracy of prediction of the heat treatment temperature of within 25° C. for the heat treatment temperature range 800° C. to 900° C.

The amount of working life used is then compared to the actual working life of a turbine blade, or turbine vane, for that particular temperature to determine if the turbine blade 28, or turbine vane 30, has any remaining working life or whether new turbine blades 28, or turbine vanes 30, need to be installed in the turbine of the gas turbine engine 10.

MARM-002 is a nickel based alloy produced by the Martin-Marietta Corporation of Bethesda, Md., USA. MARM-002 has a nominal composition of 10 wt % Co, 9 wt % Cr, 5.5 wt % Al, 10 wt % W, 2.5 wt % Ta, 1.5 wt % Ti, 1.5 wt % Hf, 0.15 wt % C and the balance Ni plus incidental impurities.

The invention is also applicable to the nickel based superalloys MARM-247 and IN738, and may be applicable to other nickel based alloys, cobalt based alloys or iron based alloys which comprise carbon and carbide forming elements, such as Cr, W, Hf etc in the form of carbide phases.

MARM-247 is a nickel based alloy produced by the Martin-Marietta Corporation of Bethesda, Md., USA. MARM-247 has a nominal composition comprising 8.3 wt % Cr, 10 wt % Co, 0.7 wt % Mo, 10 wt % W, 3 wt % Ta, 5.5 wt % Al, 1 wt % Ti, 0.14 wt % C, 1.5 wt % Hf and the balance Ni plus incidental impurities.

IN738 is a nickel based alloy and has a nominal composition comprising 16 wt % Cr, 8.5 wt % Co, 3.4 wt % Al, 2.6 wt % W, 1.7 wt % Ta, 3.4 wt % Ti, 1.7 wt % Mo, 0.8 wt % Nb, 0.1 wt % C and the balance Ni plus incidental impurities.

It is preferred that the samples are taken from the leading edge of the turbine blades 28, or turbine vanes 30, however, it may be possible to take samples from other suitable regions of the turbine blades 28, or turbine vanes 30.

Although specific ratios of the amount of carbide phases have been described it is possible to use the inverse of any of these ratios. It is also possible to use the difference of the amounts of carbide phases.

We claim:

1. A method of determining if an alloy article has any remaining working life comprising the steps of:
   (a) taking at least one sample from an alloy article, the alloy article comprising metal matrix material and carbide particles
   (b) removing substantially all metal matrix material from the at least one sample to leave the carbide particles,
   (c) analysing the carbide particles using x-ray diffraction, identifying the x-ray peaks of the main carbide phases from the x-ray diffraction spectra,
   (d) determining the ratio, or the difference, of the amount of a first carbide phase to the amount of a second carbide phase,
   (e) providing a database containing the ratio, or difference, of the first carbide phase to the second carbide phase as a function of temperature of heat treatment and time of heat treatment,
   (f) comparing the ratio, or difference, of the amount of the first carbide phase to the amount of the second carbide phase determined in step (d) with the database in step (e) to determine the temperature of heat treatment and the time of heat treatment of the sample of the alloy article,
   (g) comparing the temperature of heat treatment and the time of heat treatment of the sample of the alloy article determined in step (f) with a plurality of different heat treatment temperatures and associated heat treatment times corresponding to the full working life of the alloy article to determine if the alloy article has any remaining working life.

2. A method as claimed in claim 1 wherein step (d) comprises determining the ratio, or difference, of the amount of the $M_{23}C_6$ carbide phase to the amount of the MC carbide phase.

3. A method as claimed in claim 1 wherein step (d) comprises determining the ratio, or difference, of the amount of the $M_{23}C_6$ carbide phase to the amount of the $M_6C$ carbide phase.

4. A method as claimed in claim 1 wherein step (d) comprises determining the ratio, or difference, of the amount of the $M_6C$ carbide phase to the amount of the MC carbide phase.

5. A method as claimed in claim 1 wherein step (d) comprises determining the ratio of the integrated intensity of the x-ray peak of the first carbide phase to integrated intensity of the x-ray peak of the second carbide phase.

6. A method as claimed in claim 1 wherein step (b) comprises dissolving substantially all metal matrix material from the at least one sample in an electrochemical cell to leave the carbide particles.

7. A method as claimed in claim 6 wherein step (b) comprises dissolving substantially all the metal matrix material in an electrochemical cell having a solution comprising hydrochloric acid, tartaric acid and methanol.

8. A method as claimed in claim 1 wherein the alloy article is selected from the group comprising a nickel base superalloy, a cobalt base superalloy and an iron based superalloy.

9. A method as claimed in claim 1 wherein the alloy article is selected from the group comprising a turbine blade and a turbine vane.

10. A method as claimed in claim 9 wherein step (a) comprises removing the sample from toe leading edge of the turbine blade or turbine vane.

11. A method as claimed in claim 8 wherein the alloy article comprises an alloy comprising 10 wt % Co, 9 wt % Cr, 5.5 wt % Al, 10 wt % W, 2.5 wt % Ta, 1.5 wt % Ti, 1.5 wt % Hf, 0.15 wt % C and the balance Ni plus incidental impurities.

12. A method as claimed in claim 8 wherein the alloy article comprises an alloy comprising 16 wt % Cr, 8.5 wt % Co, 3.4 wt % Al, 2.6 wt % W, 1.7 wt % Ta, 3.4 wt % Ti, 1.7 wt % Mo, 0.8 wt % Nb, 0.11 wt % C and the balance Ni plus incidental impurities.

13. A method as claimed in claim 8 wherein the alloy article comprises an alloy comprising 8.3 wt % Cr, 10 wt % Co, 0.7 wt % Mo, 10 wt % W, 3 wt % Ta, 5.5 wt % Al, 1 wt % Ti, 0.14 wt % C, 1.5 wt % Hf and the balance Ni plus incidental impurities.

* * * * *